(12) United States Patent
Mietzner

(10) Patent No.: US 10,436,338 B2
(45) Date of Patent: Oct. 8, 2019

(54) RUPTURE DISKS FOR BIOREACTORS AND METHODS OF USING SAME

(71) Applicant: LONZA LTD, Visp (CH)

(72) Inventor: Michael Mietzner, Fremont, NH (US)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 15/836,646

(22) Filed: Dec. 8, 2017

(65) Prior Publication Data

US 2018/0163882 A1 Jun. 14, 2018

Related U.S. Application Data

(60) Provisional application No. 62/431,985, filed on Dec. 9, 2016.

(51) Int. Cl.
*F16K 17/16* (2006.01)
*C12M 1/00* (2006.01)

(52) U.S. Cl.
CPC .............. *F16K 17/16* (2013.01); *C12M 1/00* (2013.01); *C12M 23/00* (2013.01)

(58) Field of Classification Search
CPC .......... F16K 17/16; C12M 1/00; C12M 23/00
See application file for complete search history.

(56) References Cited

U.S. PATENT DOCUMENTS

| 4,071,182 A | 1/1978 | Walraven et al. |
|---|---|---|
| 4,431,018 A | 2/1984 | Finnegan |
| 4,580,589 A | 4/1986 | Le Bras et al. |
| 6,265,097 B1 | 7/2001 | Konno et al. |
| 6,589,687 B1 | 7/2003 | Konno et al. |
| 7,950,409 B2 | 5/2011 | Stokes et al. |
| 8,191,756 B2 | 6/2012 | Coppeta et al. |
| 9,470,326 B2 | 10/2016 | Goodyear et al. |
| 9,677,391 B2 | 6/2017 | Banks et al. |

(Continued)

FOREIGN PATENT DOCUMENTS

| DE | 2364269 A1 | 7/1975 |
|---|---|---|
| DE | 202008005092 U1 | 7/2008 |

(Continued)

OTHER PUBLICATIONS

International Search Report and Written Opinion for International Application No. PCT/US2017/065377 dated Apr. 5, 2018.

*Primary Examiner* — P. Macade Nichols
(74) *Attorney, Agent, or Firm* — Dority & Manning, P.A.

(57) ABSTRACT

A rupture disk includes a body including an internal wall extending from a first end of the body to a second end of the body. The internal wall defines an opening extending through the body. In some embodiments, the body further includes an internal flange formed on the internal wall, and the internal flange has a stepped surface. A rupture membrane is positioned within the body, and secured, for example, by cold welding. The rupture membrane may be secured to the stepped surface. The rupture membrane is positioned within the body such that the rupture membrane does not extend beyond the first end of the body. A process system including the rupture disk is also provided. A method of maintaining a process system that includes the rupture disk is also provided.

23 Claims, 5 Drawing Sheets

(56) References Cited

U.S. PATENT DOCUMENTS

| | | | |
|---|---|---|---|
| 2009/0120503 A1* | 5/2009 | Donahue | F16K 15/031 137/1 |
| 2015/0114478 A1* | 4/2015 | Tavard | F16K 17/16 137/14 |
| 2017/0130853 A1 | 5/2017 | Wilson et al. | |

FOREIGN PATENT DOCUMENTS

| | | | |
|---|---|---|---|
| GB | 861289 A * | 2/1961 | ............ F16K 17/16 |
| GB | 1310978 A | 3/1973 | |
| GB | 1374296 A | 11/1974 | |
| JP | 2001205452 A | 7/2001 | |
| WO | 2014095571 A1 | 6/2014 | |

* cited by examiner

RUPTURE DISKS FOR BIOREACTORS AND METHODS OF USING SAME

CROSS REFERENCE TO RELATED APPLICATIONS

This application claims the benefit of priority to U.S. Provisional Patent Application Ser. No. 62/431,985 filed on Dec. 9, 2016, which is hereby incorporated herein by reference in its entirety for all purposes.

FIELD OF THE INVENTION

The disclosure relates to rupture disks and methods of using and making the same.

BACKGROUND

The manufacture of biological products includes many processes that are conducted in closed systems or pressurized systems. In addition to bioreactors, conduits, valves, reservoirs and the like such systems typically include components that provide protection from deviations from operating pressure, e.g., over-pressurization. Rupture discs are non-reclosing pressure relief devices. They can provide relief if system pressure, e.g., vessel or bioreactor pressure, is to low or too high. Rupture discs typically provide instant response (within milliseconds) to an increase or decrease in system pressure. Once the rupture disc has ruptured it will not reseal, it is "sacrificial." Typically a rupture disk includes a one-time-use membrane that fails at a predetermined differential pressure, either positive or vacuum. A typical rupture disk is made of metal and is configured as a thin, circular membrane that is held firmly in a holder or housing, with an elastomeric member providing a hermetic seal between the rupture disk and housing.

Rupture occurs when the fluid pressure within the vessel or system exceeds the design rupture pressure of the disk. This causes fluid pressure to be relieved from the vessel or system.

In bioprocess systems, rupture disks are typically installed on a spool piece between a tank and a vent tube. Typically elastomeric members are used to seal the union of the rupture membrane and its housing.

Rupture disks are commonly used in series (upstream) with a relief valve to prevent corrosive fluids from contacting the metal parts of the valve.

SUMMARY

Sealing members, which are typically made of elastomeric materials, need periodic or event-based replacement. In particular, the need to replace, e.g., due to failure or scheduled maintenance, the elastomeric member that joins the rupture membrane to the housing of a rupture disk assembly can result in the need to replace the entire rupture disk assembly, even though the rupture disk is otherwise still serviceable. Even if the elastomeric member that joins the rupture disk to the housing could be replaced, such replacement would involve substantial manipulation of the rupture disk and could lead to premature failure of the rupture disk. Thus, replacement of the sealing member that joins the rupture disk to the housing of the rupture disk assembly typically requires replacement of the entire rupture disk assembly, including the otherwise serviceable rupture membrane and housing. It has been discovered that the sealing member that joins the rupture membrane to the housing of the rupture disk can be eliminated by providing a direct integral hermetic joint, e.g., such as is formed by cold welding, between the rupture membrane and the housing of a rupture disk assembly. The need to replace rupture disk assemblies is minimized because there is no sealing member to replace. The rupture disk assembly can still rely on sealing members to provide a seal between the rupture disk assembly and other components, e.g., tanks, but upon replacement of such sealing members the rupture disk assembly can be reused.

According to an aspect of the present disclosure, a rupture disk comprises a body including an internal wall extending from a first end of the body to a second end of the body, the internal wall defining an opening extending through the body, the body further including an internal flange formed on the internal wall, the internal flange having a stepped surface; and a rupture membrane positioned within the body, the rupture membrane including a rupture membrane surface secured to the stepped surface to form a hermetic seal, the stepped surface and the rupture membrane being positioned within the body such that the rupture membrane does not extend beyond the first end of the body.

In some embodiments, the body is configured for removable attachment to a component.

In some embodiments, the body includes a first metal and the rupture membrane is fabricated from a second metal, wherein the first metal is selected from 316L stainless steel, Inconel, indium, aluminum, copper, lead, zinc, nickel, silver, palladium, cadmium, titanium, tungsten, tin, gold, and lead, and wherein the second metal is selected from 316L stainless steel, Inconel, indium, aluminum, copper, lead, zinc, nickel, silver, palladium, cadmium, titanium, tungsten, tin, gold, and lead.

In some embodiments, the stepped surface of the internal flange and the rupture membrane surface of the rupture membrane are joined together by a metal-to-metal bond.

In some embodiments, the stepped surface of the internal flange and the rupture membrane surface of the rupture membrane are joined together by a cold weld.

In some embodiments, the rupture disk is configured to form a barrier that seals an aperture of a component to which the rupture disk is attached, and wherein the rupture membrane, prior to rupture, prevents flow of a fluid out of the aperture of the component.

In some embodiments, the aperture is greater than 10 mm.

In some embodiments, the component is suitable for use in the production of a biological product.

In some embodiments, the body is configured for attachment to a component by a connector.

In some embodiments, the component comprises a chamber or reservoir or other void, the chamber or reservoir or other void having a linear dimension of greater than 20 centimeters.

In some embodiments, the rupture disk is configured to be disposed between a first and second component, and wherein the rupture membrane, prior to rupture, forms a barrier between the first component and the second component.

In some embodiments, the body is configured as a spool piece.

In some embodiments, the body is configured so as to be removably attached by a clamp to a component.

In some embodiments, the rupture disk further comprises a gasket configured to be disposed between the first end of the body and a component and to provide a fluid-proof seal there between.

In some embodiments, the rupture membrane is positioned such that it is entirely within the body.

In some embodiments, the rupture membrane is positioned such that it is entirely within the body, but close enough to the first end of the housing to minimize a volume defined by a clean surface of the rupture membrane and a portion of the internal wall between the clean surface of the rupture membrane and the first end of the body.

In some embodiments, the rupture membrane is positioned such that it is entirely within the body such that a volume of a space defined by the face of the rupture membrane and a portion of the internal wall between the face of the rupture membrane and the first end of the body is no more than 10 cm$^3$.

In some embodiments, the internal flange and the internal wall are integrally formed.

In some embodiments, the rupture disk consists of the rupture membrane and the body formed as a spool piece.

In some embodiments, the rupture disk consists essentially of the rupture membrane and the body formed as a spool piece.

According to another aspect of the present disclosure, a process system comprises a rupture disk of the present disclosure, wherein the process system includes a bioreactor. In some embodiments, the process system is a bioprocess system.

According to another aspect of the present disclosure, a method of a method of maintaining a process system comprises detaching a rupture disk of claim 1, from a component; and reattaching the rupture disk to the component, thereby maintaining the process system. In some embodiments, the process system is a bioprocess system.

In one aspect, the disclosure features a rupture disk assembly including a housing; and a rupture membrane, wherein the rupture membrane is disposed within the housing, e.g., is integral with the housing, and the joint between the housing and rupture membrane is hermetic.

In an embodiment, the housing is configured for removable attachment to a second component, e.g., attachment by a mechanical fastener, e.g., a pressure or torque-based fastener, e.g., a bolt or clamp.

In an embodiment, the rupture disk assembly is configured for attachment to a second component with a hygienic clamp.

In an embodiment, the housing is configured for removable attachment to a second component, e.g., attachment by a mechanical fastener, e.g., a pressure or torque based fastener, e.g., a bolt or clamp.

In an embodiment, the housing is configured for attachment to a second component, by other than a weld, e.g., a cold weld.

In an embodiment, the housing is further configured for removable attachment to a third component, e.g., attachment by a mechanical fastener, e.g., a pressure or torque-based fastener, e.g., a bolt or clamp.

In an embodiment, the rupture disk assembly is further configured for attachment to a third component with a hygienic clamp.

In an embodiment, the housing is further configured for removable attachment to a third component, e.g., attachment by a mechanical fastener, e.g., a pressure or torque based fastener, e.g., a bolt or clamp.

In an embodiment, the housing is further configured for attachment to a third component, by other than a weld, e.g., a cold weld. In an embodiment, the rupture disk assembly includes a cold-welded joint between the housing and the rupture membrane. In an embodiment the rupture membrane is positioned such that it is entirely within the housing, and e.g., if concave does not protrude beyond the face of the housing.

In an embodiment the rupture membrane is positioned such that it is entirely within the housing but close enough to the face of the housing to minimize volume of the space defined by the face of the rupture membrane and the face of the housing that is adjacent a first component.

In an embodiment the rupture membrane is positioned such that it is entirely within the housing but close enough to the face of the housing such that volume of the space defined by the face of the rupture membrane and the face of the housing that is adjacent a first component is no more than 5, 10, 15, 20, 30, 40, 50, 100, 200, 300, 400, or 500 cm$^3$.

In an embodiment the rupture membrane has a diameter, or longest dimension of, 1-100 cm, 1-50 cm, 1-25 cm, 1-10 cm to 5 cm.

In an embodiment the rupture membrane has a diameter, or longest dimension of, 5-100 cm, 5-50 cm, 5-25 cm, or 5-10 cm.

In an embodiment, the housing in the rupture disk assembly comprises a metal component and the rupture membrane is metal.

In an embodiment, the metal component and the rupture membrane comprise the same metal.

In an embodiment, the metal component comprises a first metal and the rupture membrane comprises a second metal. In an embodiment, the first metal, the second metal, or both, metals comprise stainless steel (e.g., SAE 304 or SAE 316L stainless steel), carbon steel, gold, platinum, or a combination thereof.

In an embodiment, the metal component and rupture membrane are joined by cold-welding. In an embodiment, a surface of the rupture membrane and a surface of the housing are joined together by a metal-to-metal bond.

In an embodiment, the metal-to-metal bond is formed without substantial heat input, e.g., in the absence of heat that results in a molten or liquid phase at the joint in the joining, e.g., a welding process.

In an embodiment, the housing comprises a component including, e.g., a material selected from silicon, metals, ceramics, polymers, glasses, and combinations thereof.

In an embodiment, the rupture disk assembly is configured to form a barrier that seals an aperture of a second component to which the rupture disk assembly is attached and prior to rupture prevents flow of a fluid, e.g., a liquid or gas, or mixture of a liquid and a gas, out of the second component.

In an embodiment, the second component comprises a vessel, e.g., a pressure vessel.

In an embodiment, the second component comprises a vessel required by law, statute, rule or regulation, to have a pressure relief component.

In an embodiment, the rupture disk assembly includes an aperture greater than 2, 3, 4, 5, 10, 15, or 20 mm.

In an embodiment, the second component is a component used in the production of a biological product, e.g., a polypeptide, e.g., a component or biological product described herein.

In an embodiment, the second component comprises a chamber or reservoir in liquid communication with the rupture membrane, e.g., the chamber or reservoir vessel.

In an embodiment, the chamber or reservoir vessel has a capacity or volume of at least 0.1, 0.5, 1.0, 10, 20, 30, 40, 50, 100, 200, 500, 1,000, 1,500, 10,000, 12,500, 15,00, 17,500, 20,000, 25,000 or 30,000 L.

In an embodiment, the second component comprises a wall or housing, e.g., defining at least a portion of the chamber or reservoir. In an embodiment, the thickness of the wall or housing is greater than 1, 10, 5, 10, 15, or 20 mm.

In an embodiment, the housing of the rupture disk assembly is configured for attachment to the second component by a joint that is not integral, e.g., a joint that including a sealing member, e.g., a deformable member, e.g., a gasket, e.g., an elastomeric gasket.

In an embodiment, the second component comprises a chamber or reservoir or other void, the chamber or reservoir or other void having a linear dimension, e.g., depth, diameter or radius, of greater than 3, 4, 5, 10, 20, 30, 50, 100 centimeters.

In an embodiment, the rupture disk assembly is configured so as to be disposed between a first and second component and wherein the rupture membrane, prior to rupture, forms a barrier between the second component and a third component.

In an embodiment, the rupture disk assembly is configured so as to be disposed between a second and third component. In an embodiment, the rupture membrane, prior to rupture, prevents flow of fluid, e.g., a liquid or gas, or mixture of a liquid and a gas, from the second component into the third component.

In an embodiment, the second or third component of the rupture disk assembly, e.g., a vessel, has a capacity or volume of at least 0.1, 0.5, 1.0, 10, 20, 30, 40, 50, 100, 200, or 500 liters of liquid.

In an embodiment, the housing is configured as a spool piece.

In an embodiment, the housing of the rupture disk assembly is configured as a cylinder having a lumen and the rupture membrane is disposed so as to separate a first portion of the lumen from a second portion of the lumen.

In an embodiment, the housing of the rupture disk assembly is configured so as to be attached to a second component, e.g., a vessel, e.g., a tank, or a pipe.

In an embodiment, the housing of the rupture disk assembly is not welded to a second component, e.g., a vessel, e.g., a tank, or a pipe.

In an embodiment, the housing of the rupture disk assembly is configured so as to be removably attached, e.g., attached by a bolt, clamp, or other removable fastener, to a second component, e.g., a vessel, e.g., a tank, or a pipe.

In an embodiment, the housing of the rupture disk assembly is configured for disposition or placement of a sealing member, e.g., a deformable member, e.g., a gasket, e.g., an elastomeric gasket, between the housing and a second component.

In an embodiment, the housing of the rupture disk assembly is configured for disposition or placement of a sealing member, e.g., a deformable member, e.g., a gasket, e.g., an elastomeric gasket, between the housing and a third component.

In an embodiment, the housing of the rupture disk assembly is configured to be attached, e.g., by a fastener, e.g., by a clamp or bolt, to a second component, e.g., a conduit or pipe, pipe spool, flange, a valve, a reversible pressure regulator, a heat exchanger, or a vessel, e.g., a bioreactor.

In an embodiment, the rupture disk assembly further comprises a sealing member, e.g., a deformable member, e.g., a gasket, e.g., an elastomeric gasket, configured to be disposed between the housing and the second component and provide a fluid-proof seal there between.

In an embodiment, the housing of the rupture disk assembly is integral with e.g., welded to, a second component, e.g., a conduit or pipe, pipe spool, flange, a valve, a reversible presser regulator, or a vessel, e.g., a bioreactor, provided that the second component has a capacity or volume of at least 0.1, 0.5, 1.0, 10, 20, 30, 40, 50, 100, 200, or 500 liters of liquid or is attached directly or indirectly to another component having such volume or capacity.

In an embodiment, the rupture disk assembly further comprises a packaging component configured so as to protect the rupture membrane from damage or unwanted contact with other objects. Typically, the packaging component protects the pressure-side face of the rupture membrane. For example, the rupture disk assembly can comprise a cap, e.g., a polymeric or plastic cap, configured to fit over the aperture of the housing nearest the rupture membrane. The cap can be configured so as to fit tightly but removably from the rupture disk assembly. The rupture disk assembly can comprise a second cap configured and placed so as to protect the non-pressure-side face of the rupture membrane.

In an embodiment, the rupture disk assembly of the process system is disposed between a first component and a second component.

Also provided is a process system including a rupture disk assembly as described above, and a second component, e.g., a second component described herein, e.g., wherein the rupture disk assembly and the second component are in fluid connection.

In an embodiment of the process system, the second component comprises a vessel, e.g., a bioreactor, a conduit, e.g., a pipe, a valve, e.g., a reversible pressure regulator, an element for providing a readout of pressure, e.g., upstream or downstream of the rupture disk assembly.

In an embodiment of the process system, the second component, e.g., a vessel, has a capacity or volume of at least 0.1, 0.5, 1.0, 10, 20, 30, 40, 50, 100, 200, or 500 liters, of liquid.

In an embodiment of the process system, the rupture disk assembly is attached to a second component.

In an embodiment of the process system, the rupture disk assembly is attached to a second component by a mechanical fastener, e.g., by clamps or bolts.

In an embodiment, the process system further includes a sealing member, e.g., a deformable member, e.g., a gasket, e.g., an elastomeric gasket, disposed between the housing and the second component.

In an embodiment, the process system includes a rupture disk assembly with a housing that is integral with. e.g., welded to, a second component, e.g., a bioreactor, a conduit, e.g., a pipe, a valve, e.g., a reversible pressure regulator, an element for providing a readout of pressure, e.g., upstream or downstream of the rupture disk assembly, provided that the second component has a capacity or volume of at least 0.1, 0.5, 1.0, 10, 20, 30, 40, 50, 100, 200, or 500 liters of liquid or is attached directly or indirectly to another component having such volume or capacity.

In an embodiment, the process system includes a second component that comprises a vessel, e.g., a bioreactor. In an embodiment, the second component comprises a valve, e.g., a reversible pressure regulator.

In an embodiment, one or both of the second and third component is directly attached to the rupture disk assembly.

In an embodiment, a fourth component is disposed between the rupture disk assembly and the second or third component.

Also provided is a method of making a rupture disk assembly that includes forming a direct (e.g., lacking a third component such as an elastomer) hermetic joint between a rupture membrane and a housing, thereby making a rupture disk assembly.

In an embodiment, the method includes forming a cold-weld joint between the rupture disk membrane and the housing.

In an embodiment, the rupture disk assembly is a rupture disk assembly as herein described.

In an embodiment, the housing is configured for removable attachment to a second component, e.g., attachment by a mechanical fastener, e.g., a pressure or torque-based fastener, e.g., a bolt or clamp.

In an embodiment, the rupture disk assembly is configured for attachment to a second component with a hygienic clamp.

Also provided by the disclosure is a method of maintaining a process system, e.g., a process system as herein described, comprising detaching a rupture disk assembly, e.g., a rupture disk assembly as herein described, from a second component, e.g., a vessel, e.g., a reactor vessel, and, optionally, inspecting, maintaining, or replacing a sealing member disposed between the rupture disk assembly and the second component. The method further includes reattaching the rupture disk assembly to a second component, e.g., the second component from which it was detached, thereby maintaining a process system.

Also provided the disclosure is a method of making a rupture disk assembly that includes forming a direct (e.g., lacking a third component such as an elastomer) hermetic joint between a rupture membrane and a housing, thereby making a rupture disk assembly.

In an embodiment, the method includes forming a cold-weld joint between the rupture disk membrane and the housing.

In an embodiment, the rupture disk assembly is a rupture disk assembly as herein described.

In another aspect, the disclosure provides a method of replacing a gasket or sealing member-based rupture disk, comprising identifying a rupture disk or rupture disk assembly to be replaced; removing the to-be-replaced rupture disk or rupture disk assembly, and installing a new rupture disk assembly.

Also provided by the disclosure is a method of maintaining a process system, e.g., a process system as herein described, comprising detaching a rupture disk assembly, e.g., a rupture disk assembly as herein described, from a second component, e.g., a vessel, e.g., a reactor vessel, and, optionally, inspecting, maintaining, or replacing a sealing member disposed between the rupture disk assembly and the second component. The method further includes reattaching the rupture disk assembly to a second component, e.g., the second component from which it was detached, thereby maintaining a process system.

DETAILED DESCRIPTION

Figure 1:
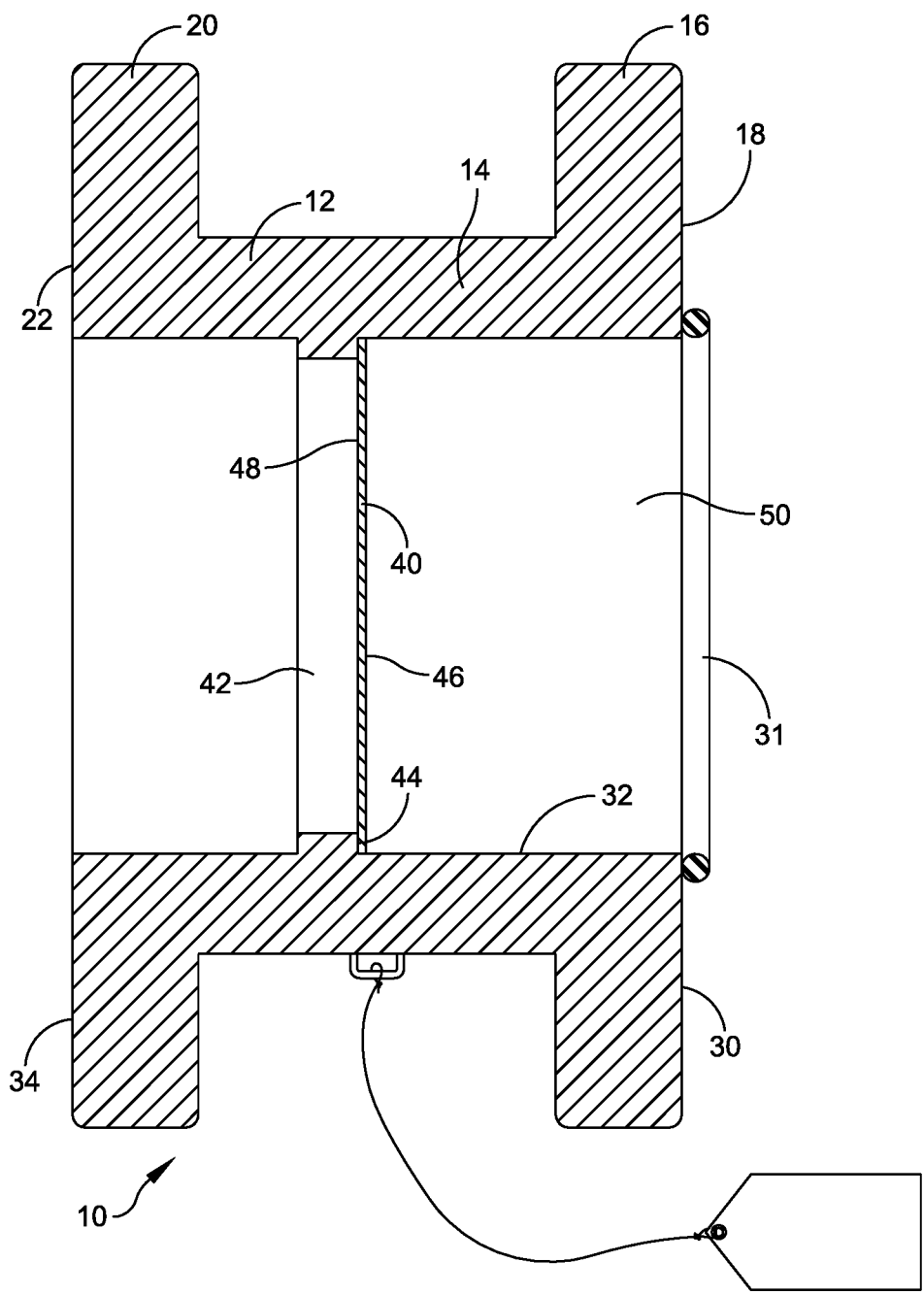
FIG. 1 is a cross-sectional view of an embodiment of a rupture disk assembly.

The invention provides rupture disk assemblies that provide a seal between the rupture disk or membrane and a housing that is integral and does not include a separated sealing member, and methods of making and using the same. In embodiments the rupture disk assembly is not integral with the vessel, e.g., tank, it protects.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting. The articles "a" and "an" are used herein to refer to one or to more than one (i.e., to at least one) of the grammatical object of the article. By way of example, "a cell" can mean one cell or more than one cell.

As used herein, "cold welding" refers to a process of joining a first and a second metal surface without fusion/heating and without the production of a liquid or molten phase at the site of the weld. Typically, mating the two surfaces at high pressure plays a key role in cold welding.

As used herein, the term "hermetic seal or joint" refers to seal that prevents a fluid, e.g., a liquid or gas, from passing.

As used herein a "rupture disk or membrane" refers to a device which, prior to reaching the failure pressure, obstructs the path of a liquid. At failure pressure, the device opens (by irreversible cleavage or separation-based failure) to allow flow of the liquid. In an embodiment the rupture disk ruptures or fails at a predetermined differential pressure, either positive or vacuum.

As used herein, the terms "peptide," "polypeptide," and "protein" are used interchangeably, and refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

"Product" as that term is used herein refers to a molecule, nucleic acid, polypeptide, or any hybrid thereof, that is produced, e.g., expressed, by a cell which has been modified or engineered to produce the product. In one embodiment, the product is a naturally occurring product or a non-naturally occurring product, e.g., a synthetic product. In one embodiment, a portion of the product is naturally occurring, while another portion of the product is non-naturally occurring. In one embodiment, the product is a polypeptide, e.g., a recombinant polypeptide. In one embodiment, the product is suitable for diagnostic or pre-clinical use. In another embodiment, the product is suitable for therapeutic use, e.g., for treatment of a disease. In one embodiment, the modified or engineered cells comprise an exogenous nucleic acid that controls expression or encodes the product. In other embodiments, the modified or engineered cells comprise other molecules, e.g., that are not nucleic acids, that controls the expression or construction of the product in the cell.

"Recombinant polypeptide" or "recombinant protein" as those terms are used herein refer to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering (of the cell or of a precursor cell). E.g., at least one nucleotide was altered, e.g., it was introduced into the cell or it is the product of a genetically engineered rearrangement. In an embodiment, the sequence of a recombinant polypeptide does not differ from a naturally occurring isoform of the polypeptide or protein. In an embodiment, the amino acid sequence of the recombinant polypeptide differs from the sequence of a naturally occurring isoform of the polypeptide or protein. In an embodiment, the recombinant polypeptide and the cell are from the same species. In an embodiment, the recombinant polypeptide is endogenous to the cell, in other words, the cell is from a first species and the recombinant polypeptide is native to that first species. In an embodiment, the amino acid sequence of the recombinant polypeptide is the same as or is substantially the same as, or differs by no more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% from, a polypeptide encoded by the endogenous genome of the cell. In an embodiment, the recombinant polypeptide and the cell are from different species, e.g., the recombinant polypeptide is a human polypeptide and the cell is a non-human, e.g., a rodent, e.g., a CHO, or an insect cell. In an embodiment, the recombinant polypeptide is exogenous to the cell, in other words, the cell is from a first species and the recombinant polypeptide is from a second species. In one embodiment, the polypeptide is a synthetic polypeptide. In one embodiment, the polypeptide is derived from a non-naturally occurring source. In an embodiment, the recombinant polypeptide is a human polypeptide or protein which does not differ in amino acid sequence from a naturally occurring isoform of the human polypeptide or protein. In an embodiment, the recombinant polypeptide differs from a naturally occurring isoform of the human polypeptide or protein at no more than 1, 2, 3, 4, 5, 10, 15 or 20 amino acid residues. In an embodiment, the recombinant polypeptide differs from a naturally occurring isoform of the human polypeptide by no more than 1, 2, 3, 4, 5, 6, 7, 8, 9, 10, or 15% of its amino acid residues. As used herein a "hygienic clamp" or "sanitary clamp", refers to a clamp configured to attach a rupture disk assembly to another component, wherein the clamp prevents exposure of the contents of the fluid (liquid or gas) flowing through the rupture disk assembly to the exterior. Exemplary hygienic clamps include sanitary, leak-proof fittings known in the art, including the TRI-CLOVER® fitting sold by Alfa Laval, Inc. (Richmond, Va. USA). In embodiments, the hygienic clamp has dimensions disclosed in ASME Table DT-5-2 ("Hygienic Clamp Ferrule Standard Dimensions and Tolerances", 2009), which is incorporated herein by reference in its entirety.

Rupture Disk Assemblies

Figure 2:
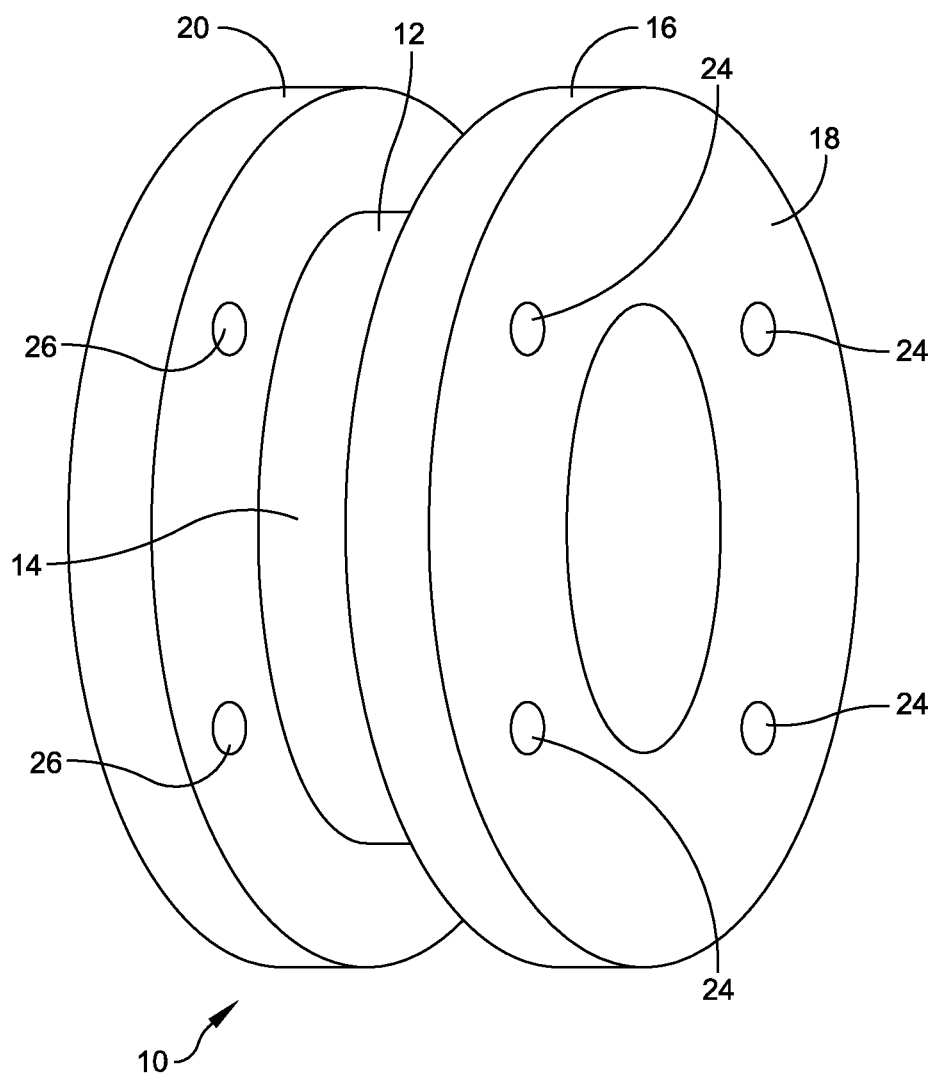
FIG. 2 is a perspective view of an embodiment of the rupture disk assembly.

One embodiment of a rupture disk assembly (or rupture disk) 10 is depicted and generally indicated in the cross-section of FIG. 1 and in the perspective view in FIG. 2. As shown, the rupture disk assembly 10 includes a housing 12 that is configured with a body portion 14, a first flange 16 that has a first face 18, and a second flange 20 that has a second face 22. Each of the first face 18 and the second face 22 is suitable for attaching the rupture disk 10 to other components. The first face 18 can include one or more openings 24 and the second face 22 can include one or more openings 26 for attaching the rupture disk assembly 10 to other components, including other components not shown in FIGS. 1 and 2. For example, the body portion 14 is configured for removable attachment to a component, such as a bioprocess container. In some embodiments, the body portion 14 is configured to be attached to a component by a connector, such as a clamp, a sanitary clamp, a bolt, a pressure-based fastener, a torque-based fastener, a hygienic clamp, a mechanical fastener, or another fastener.

The first face 18 and the second face 22 are each suitable for mating with an elastomeric sealing member, such as an elastomeric o-ring, to provide a seal between the rupture disk assembly 10 and one or more components to which the rupture disk assembly 10 is attached. In some embodiments, the body portion 14 is configured to be removably attached by a clamp to a component. In some embodiments, a sealing member, is disposed between a first end 30 of the body portion 14 and a component to which the body portion 14 is attached to provide a fluid-proof seal between the body portion 14 and the component to which the body portion 14 is attached. In some embodiments, the sealing member may be a gasket 31 configured to be disposed between the first end 30 of the body portion 14 and a component to which the rupture disk 10 is secured, and to provide a fluid-proof seal there between.

The body portion 14 includes an internal wall 32 that extends from the first end 30 of the body portion 14 to a second end 34 of the body portion 14. The internal wall 32 defines an opening that extends through the body portion 14. In some embodiments, the internal wall 32 defines a straight bore opening that extends through the body portion 14.

The internal wall 32 is configured to support a rupture membrane 40. In FIG. 1, the body portion 14 includes an internal flange 42 that is formed on the internal wall 32. The internal flange 42 may be formed, for example, by machining the internal wall 32 and the internal flange 42 when forming the body portion 14. In other embodiments, the internal flange 42 may be secured to the internal 32 wall of the body portion 14, for example by cold welding, to form a hermetic seal between the internal flange 42 and the body portion 14. The internal flange 42 has a stepped surface 44 that is configured to support the rupture membrane 40, as described further herein.

In some embodiments, the internal flange 42 and the internal wall 32 are integrally formed. In some embodiments, the internal flange 42 and the internal wall 32 are an integral structure. In some embodiments, the internal flange 42 and the internal wall 32 can be formed from a single piece of a material.

In some embodiments, the rupture disk 10 consists of a rupture membrane 40 and a housing 12 formed as a spool piece. In some embodiments, the rupture disk 10 consists essentially of a rupture membrane 40 and a housing 12 formed as a spool piece.

The rupture membrane 40 may be circular or non-circular when viewed from an end of the body portion 14. In some embodiments, when viewed from an end of the body portion 14, the rupture membrane 40 has a diameter, or longest dimension of, 1-100 centimeters (cm), 1-50 cm, 1-25 cm, 1-10 cm, or 1-5 cm. In some embodiments, when viewed from an end of the body portion 14, the rupture membrane 40 has a diameter, or longest dimension of, 5-100 cm, 5-50 cm, 5-25 cm, or 5-10 cm.

In some embodiments, the body portion 14 is fabricated from a first metal. In some embodiments, the first metal may be selected from Hastelloy®, nickel, duplex stainless steel, SAE 316L stainless steel, SAE 304 stainless steel, carbon steel, platinum, Inconel, stainless steel indium, aluminum, copper, lead, zinc, nickel, silver, palladium, cadmium, titanium, tungsten, tin, gold, lead, or another metal, or another combination of these or other metals.

In some embodiments, the body portion 14 of the housing 12 is configured as a spool piece. The rupture disk 10 can be easily installed and removed from a system. When the rupture membrane 40 ruptures, for example due to a sudden pressure spike, the rupture disk 10 can be easily replaced.

Similarly, when a user needs to replace a sealing member positioned between the rupture disk 10 and a component to which the rupture disk 10 is secured, the user can simply remove the rupture disk 10 from the component, remove the sealing member, put a new sealing member in place of the old sealing member, and re-secure the same rupture disk 10 to the component.

Sealing members, which are typically made of elastomeric materials, need periodic or event-based replacement. According to embodiments of the present disclosure, there is no need to replace an old rupture disk, such as the rupture disk 10, with a new rupture disk, such as the rupture disk 10, simply due to the need to replace the sealing member. This allows a user to install a rupture disk 10 for the full extent of the rated lifetime of the rupture disk 10, which may be based on factors such as the ability of the rupture membrane 40 to endure cyclic loading.

There is no elastomer, such as a gasket, between the rupture membrane 40 and the housing 12. In some embodiments, because there is no gasket between the rupture membrane 40 and the housing 12, all gaskets or other sealing members that directly engage the rupture disk 10 can be replaced without the need to reposition the rupture membrane 40 with respect to the housing 12. This ensures that a seal between the rupture membrane 40 and the housing 12 is maintained after replacement of the sealing member(s).

In some embodiments, the rupture disk 10 can be incorporated into any typical manufacturing and clean room equipment. In some embodiments, the rupture disk 10 is fully suitable for cGMP (current good manufacturing practice) processes.

The rupture disk 10 is configured to be disposed between a first and second component. In some embodiments, the first component may be a unit for bioprocessing and the second component may be a reservoir. The rupture membrane 40, prior to rupture, forms a barrier between the first component and the second component. In some embodiments, the rupture disk 10 is configured to be disposed on a first component, with an opening on the rupture disk 10 that is open to the atmosphere, so that the rupture disk 10, prior to rupture, forms a barrier between the first component and the atmosphere.

The rupture membrane 40 is positioned within the body portion 14. A first surface 46 of the rupture membrane 40 faces in a first direction, which is the direction towards the first end 30 of the body portion 14. The first surface 46 of the rupture membrane 40 is provided as a clean surface. In some embodiments, the clean surface is free of crevices. In some embodiments, the clean surface is configured for engaging a biological product during a biological process, such as a biological manufacturing process. A second surface 48 of the rupture membrane 40 faces in a second direction, which is the direction towards the second end 34 of the body portion 14.

In some embodiments, the stepped surface 44 of the internal flange 42 and the second surface 48 of the rupture membrane 40 are joined together by a metal-to-metal bond. In some embodiments, the metal-to-metal bond is formed in the absence of heat that results in a molten or liquid phase at the joint during a joining process. In some embodiments, the stepped surface 44 of the internal flange 42 and the second surface 48 of the rupture membrane 40 are joining surfaces that are joined together by a cold weld. In some embodiments, the stepped surface 44 of the internal flange 42 and the second surface 48 of the rupture membrane 40 are joined together by another method. In some embodiments, the stepped surface 44 of the internal flange 42 and the second surface 48 of the rupture membrane 40 are joined together by electron-beam welding.

In FIG. 1, the rupture membrane 40 is positioned against the internal flange 42, and is cold welded to the internal flange 42. In particular, the second surface 48 of the rupture membrane 40 is secured by cold welding to the stepped surface 44 of the internal flange 42 to form a hermetic seal between the rupture membrane 40 and the body portion 14.

In some embodiments, the rupture membrane 40 is cold welded to the internal wall 32 of the body portion 14.

The stepped surface 44 and the rupture membrane 40 are positioned within the body portion 14 such that the rupture membrane 40 does not extend beyond the first end 30 of the body portion 14 of the housing 12. In some embodiments, as shown in FIG. 1, the rupture membrane 40 is configured such that it does not extend outside of the housing 12 at either end of the body portion 14 of the housing 12.

Generally, the rupture membrane 40 is disposed to minimize a volume of dead space 50 when the face 18 of rupture disk assembly 10 is mated with another component, such as a bioprocessing unit. In FIG. 1, the rupture membrane 40 is positioned such that it is entirely within the space defined by the internal wall 32 of the body portion 14. More particularly, the rupture membrane 40 is positioned such that it is entirely within the body portion 14, but close enough to the first end 30 of the body portion 14 of the housing 12 to minimize the volume of dead space 50 defined by the first surface 46 of the rupture membrane 40 and a portion of the internal wall 32 of the body portion 14 between the first surface 46 of the rupture membrane 40 and the first end 30 of the body portion 14. When the rupture disk 10 is secured to a component, a surface of that component would be flush with the first face 18 of the first flange 16 of the housing 12.

In some embodiments, the rupture membrane 40 is positioned such that it is entirely within the body portion 14 such that the volume of the dead space 50 defined by the first surface 46 of the rupture membrane 40 and the portion of the internal wall 32 between the first face 46 of the rupture membrane and the first end 30 of the body portion 14 that is adjacent a first component is no more than 10 cm$^3$. In some embodiments, the volume of the dead space 50 defined by the first surface 46 of the rupture membrane 40 and the portion of the internal wall 32 between the first face 46 of the rupture membrane 40 and the first end 30 of the body portion 14 that is adjacent a first component is no more than 5, 10, 15, 20, 30, 40, 50, 100, 200, 300, 400, or 500 cm$^3$.

In some embodiments, the rupture membrane 40 is fabricated from a second metal. In some embodiments, the second metal of the rupture membrane 40 is different from the first metal of the body portion 14. For example, the second metal may be selected from Hastelloy®, nickel, duplex stainless steel, SAE 316L stainless steel, SAE 304 stainless steel, carbon steel, platinum, Inconel, stainless steel indium, aluminum, copper, lead, zinc, nickel, silver, palladium, cadmium, titanium, tungsten, tin, gold, lead, or another metal, or another combination of these or other metals In some embodiments, the rupture membrane 40 is scored on the first surface 46 and/or the second surface 48 of the rupture membrane 40. In some embodiments, the rupture membrane 40 is configured to rupture at a specific pressure. In some embodiments, the rupture membrane 40 can be exposed to repeated pressurization cycles before needing to be replaced.

The rupture disk 10 is configured to form a barrier that seals an aperture of a component to which the body portion 14 of the rupture disk 10 is attached. In some embodiments, the rupture disk 10 forms a hermetic seal of an aperture of a component to which the body portion 14 of the rupture disk 10 is attached. The rupture membrane 40, prior to rupture, prevents flow of a fluid out of the aperture of the component to which the body portion 14 of the rupture disk 10 is attached. In some embodiments, the aperture is greater than 10 mm. In some embodiments, the component is suitable for use in the production of a biological product. In some embodiments, the component comprises a chamber or reservoir or other void, and the chamber or reservoir or other void has a linear dimension of greater than 20 centimeters.

Figure 3A:
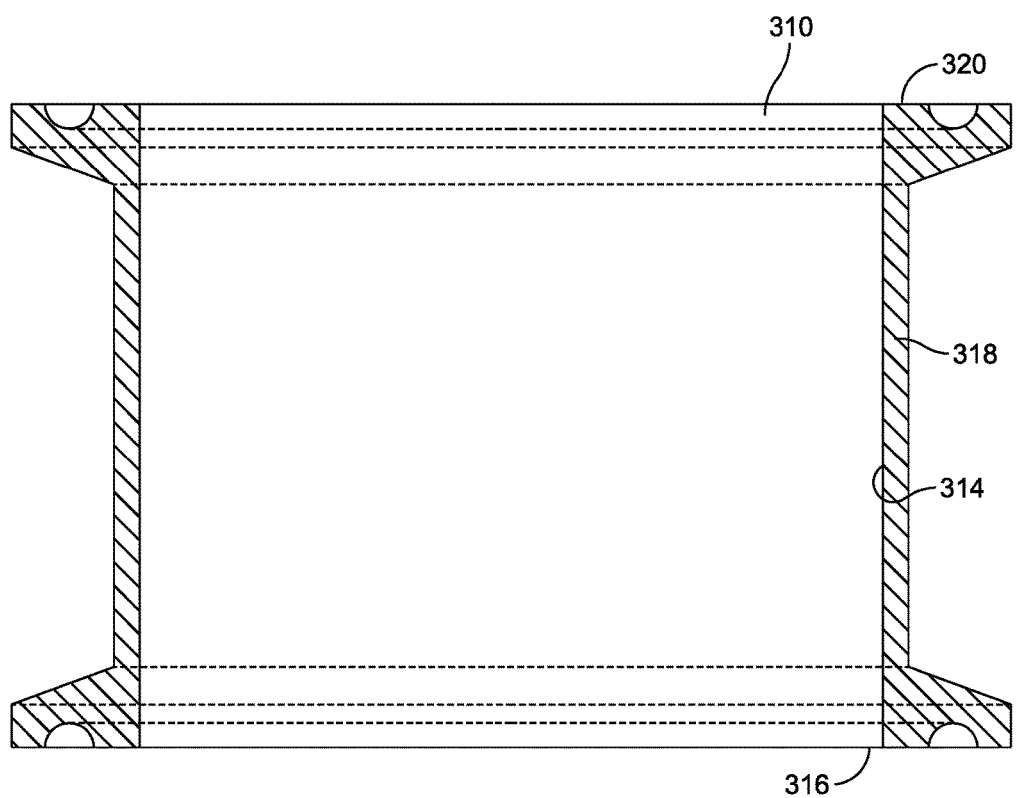
FIG. 3A shows a rupture disk housing.
Figure 3B:
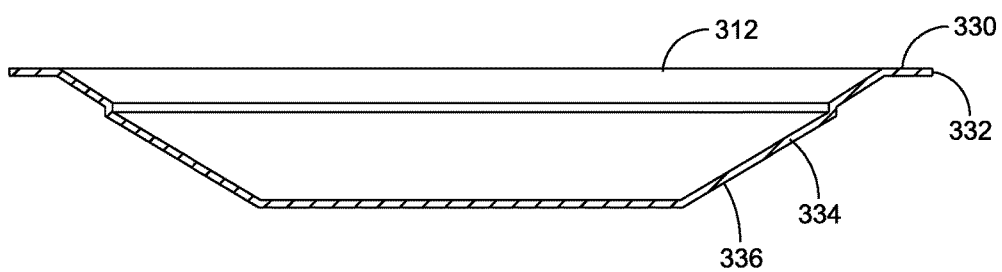
FIG. 3B shows a rupture membrane carrier.
Figure 3C:
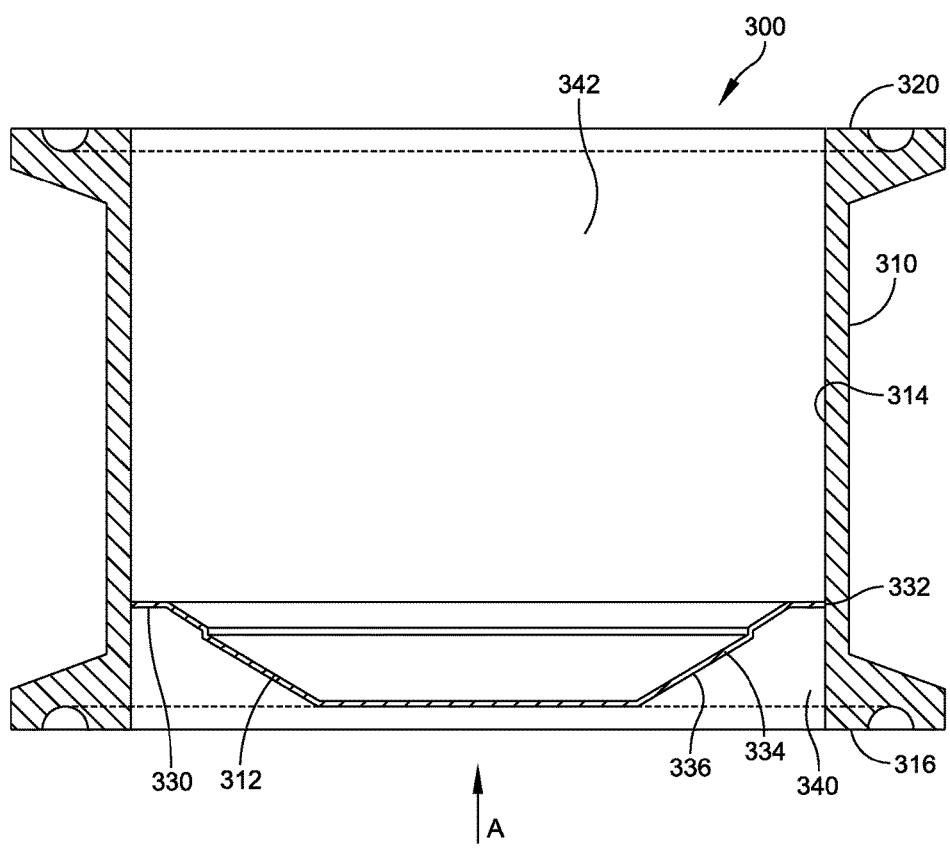
FIG. 3C shows the rupture membrane carrier secured within the rupture disk housing to form an assembled rupture disk assembly.

According to an aspect of the present disclosure, FIGS. 3A-3C depict an embodiment of a rupture disk assembly shown generally at 300. The rupture disk assembly 300 includes a rupture disk housing 310 and a rupture membrane carrier 312. FIG. 3A shows the rupture disk housing 310. FIG. 3B shows the rupture membrane carrier 312. FIG. 3C shows the rupture membrane carrier 312 secured within the rupture disk housing 310 to form the assembled rupture disk assembly 300.

The rupture disk housing 310 includes a body portion 318 having an internal wall 314 that extends from a first end 316 of the body portion 318 of the rupture disk housing 310 to a second end 320 of the body portion 318 of the rupture disk housing 310. The internal wall 314 defines an opening extending through the body portion 318 of the rupture disk housing 310. In some embodiments, the body portion of the rupture disk housing 310 includes an internal flange formed on the internal wall 314. In some embodiments, the internal flange has a stepped surface.

The rupture membrane carrier 312 includes an outer flange portion 330 that is annular and that terminates at an outer edge 332 of the rupture membrane carrier 312. The rupture membrane carrier 312 is positioned within the body portion of the rupture disk housing 310 in FIG. 3C. The outer edge 332 of the rupture membrane carrier 312 is secured to the internal wall 314 of the rupture membrane carrier 312 to form a hermetic seal between the rupture membrane carrier 312 and the rupture disk housing 310. In some embodiments, the outer edge 332 of the rupture membrane carrier 312 is secured to the internal wall 314 of the rupture membrane carrier 312 by cold welding to form a hermetic seal between the rupture membrane carrier 312 and the rupture disk housing 310. In such embodiments, the outer edge 332 includes a first joining surface and the internal wall 314 includes a second joining surface in the cold welding process.

In some embodiments, the rupture membrane carrier 312 includes a rupture membrane carrier surface that is secured to a stepped surface on an internal flange on the rupture disk housing 310 to form a hermetic seal, and the stepped surface and the rupture membrane are positioned within the body such that the rupture membrane does not extend beyond the first end of the body.

The rupture membrane carrier 312 includes a rupture membrane portion 334 that has a first rupture membrane surface 336, which is convex. The convex first rupture membrane surface 336 is oriented to face a fluid, such as a bioprocess fluid, which exerts a pressure in direction A on the first rupture membrane surface 336.

A volume 340 defined by the first rupture membrane surface 336 and the portion of the internal wall 314 between the first rupture membrane surface 336 and the first end 316 of the body portion of the rupture disk housing 310 is minimized.

The volume 340 is a clean volume, which is configured to contain a bioprocess fluid during processing of the bioprocess fluid. In some embodiments, the convex first rupture membrane surface 336 is free of crevices, and the internal wall 314 is free of crevices.

On the opposite side of the rupture membrane portion 334 from the volume 340 is a non-pressure volume 342. In typical operation, the non-pressure volume 342 does not contact the bioprocess fluid until the rupture membrane portion 334 ruptures.

The first rupture membrane surface 336, the internal wall 314, and the cold weld between the rupture membrane carrier 312 and the rupture disk housing 310 provide surfaces that are free of crevices. The rupture disk assembly 300 is configured for use in bioprocessing, and in other clean environments.

In some embodiments, the rupture disk assembly 10 or the rupture disk assembly 300 further includes a packaging component configured to protect the rupture membrane 80 or the rupture membrane portion 334 from damage or unwanted contact with other objects. Typically, the packaging component protects the pressure-side face of the rupture membrane, which is the first surface 46 in FIG. 1 and is the first rupture membrane surface 336 in FIG. 3C. For example, the rupture disk assembly can include a cap, e.g., a polymeric or plastic cap, configured to fit over the aperture of the housing nearest the rupture membrane. The cap can be configured to fit tightly but removably from the rupture disk assembly. The rupture disk assembly can include a second cap configured and placed so as to protect the non-pressure-side face of the rupture membrane.

According to another aspect of the present disclosure, a process system includes a rupture disk according to any of the embodiments described above and a second component. The rupture disk and the second component are in fluid connection. In some embodiments, the process system includes a bioreactor. In some embodiments, the process system is a bioprocess system.

In some embodiments, the second component comprises a chamber or reservoir in liquid communication with the rupture disk. In some embodiments, the chamber or reservoir vessel has a capacity or volume of at least 0.1, 0.5, 1.0, 10, 20, 30, 40, 50, 100, 200, 500, 1,000, 1,500, 10,000, 12,500, 15,00, 17,500, 20,000, 25,000 or 30,000 L. In some embodiments, the second component comprises a wall or housing, such as a wall or housing defining at least a portion of the chamber or reservoir. In some embodiments, the thickness of the wall or housing is greater than 1, 10, 5, 10, 15, or 20 mm.

According to another aspect of the present disclosure, a method of maintaining a process system is provided. In some embodiments, the method includes a step of detaching a rupture disk of any of the embodiments described above from a second component. The method then includes reattaching the rupture disk to a component, such as the second component from which the rupture disk was detached, thereby maintaining a process system. In some embodiments, the process system is a bioprocess system. A bioprocess system may include a bioreactor or processing system, such as the reactors and/or components discussed herein.

With reference to FIG. 1, in an embodiment, the rupture disk assembly 10 is provided on a vessel e.g., a processing tank, having a port configured for attachment to the rupture disk assembly 10. In an embodiment the port comprises a sanitary ferrule configured to allow attachment of the rupture disk assembly 10, e.g., by use of a sanitary clamp.

With reference to FIG. 1, in an embodiment, the rupture disk assembly 10 is disposed within the housing 12. In an embodiment, the rupture disk is positioned deeply enough within the housing 12 that it does not protrude beyond the housing 12. In an embodiment, the rupture disk is recessed below the face of the housing. In an embodiment, the rupture disk assembly 10 is positioned, e.g., to facilitate cleaning, provided it is positioned deeply enough so as not to protrude into the space or volume between the pressure-side surface of the rupture disk and the housing.

The rupture disk 10 or the rupture disk 300 may be configured for use with other components that comprise systems that have one of various specialized applications such as one or more of, but not limited to: sterile reception/storage of cells; automated mixing and delivery of reagents for protein expression, production, modification (e.g., post-translational modification) and/or secretion; automated monitoring protein expression, production, modification, and/or secretion; cell sorting and selection, including safe waste collection; cell washing and cell collection; cell seeding on or within a proliferation substrate or scaffold; automated mixing and delivery of proliferation reagents; proliferation of cells to expand cell populations; automated monitoring of cell conditions, including detection of confluence or growth phase; controlled cell release from the proliferation substrate or scaffold; repeated proliferation steps on selected surface area sizes to increase cell numbers; cell seeding on or within culture scaffold or matrix; automatic monitoring of cell/tissue culture conditions; automatic monitoring of protein expression or secretion; mechanical and/or biochemical stimulation to promote proliferation; purification of the protein and/or recovery of the protein; and storage and transportation of cells and/or protein product.

A culture vessel may be rotated or agitated within the overall device via control actuators. Rotation may enable the beneficial use of gravity to effect specific bioprocessing sequences such as sedimentation-based cell seeding and fluid exchange within the bioreactor.

In embodiments, the system comprises a vessel having a housing having one or more inlet ports and one or more outlet ports for media flow and at least one chamber defined within said bioreactor housing for receiving cells and facilitating cell culture and protein production. The chamber may be selected from the group consisting of a cell culture/proliferation chamber and/or protein production chamber. Furthermore, the chamber houses one or more substrates and/or scaffolds. In embodiments of the disclosure, the two chambers may be provided operably connected within the bioreactor and be operably connected. Alternatively, the two chambers may be independently operable or co-operatively operable. In still further aspects, the chambers and/or bioreactors are operably connected to provide for the exchange of fluids, cells and/or tissues between the chambers and/or bioreactors. The scaffold for use in the present disclosure is selected from the group consisting of a porous scaffold, a porous scaffold with gradient porosity, a porous reticulate scaffold, a fibrous scaffold, a membrane encircled scaffold and combinations thereof. Funnels or similar passageways may be provided between chambers within a bioreactor. Furthermore, one or more filters may be provided at any location within a bioreactor.

The cell culture device described herein in various embodiments is under the control of one or more microprocessors that may be preprogrammed in order that the user can select a specific type of environment (or sequence of environments) within the bioreactor such as cell proliferation, cell maintenance, protein production, or protein secretion. This eliminates operator intervention and reduces the possibility of inadvertent contamination.

Cold Welding

Cold welding, or contact welding, is a solid-state welding process in which joining takes place without fusion/heating at the interface of the two parts to be welded. Unlike in fusion-welding processes, in embodiments, no liquid or molten phase is present when the joint or weld is formed.

Cold welding has traditionally been associated with joining metal surfaces under ambient vacuum and/or contacting them with relatively large force, e.g., pressing them together at high pressure. For example, it was first recognized as a general materials phenomenon in the 1940s with the discovery that two clean, flat surfaces of similar metal would strongly adhere if brought into contact under vacuum.

Cold welding methods suitable for use in, or which can be adapted for use in, methods and devices disclosed herein are described in, e.g., U.S. Pat. No. 8,191,756. In an embodiment a first substrate having at least one first joint structure which comprises a first joining surface, which surface comprises a first metal; providing a second substrate having at least one second joint structure which comprises a second joining surface, which surface comprises a second metal; and compressing together the at least one first joint structure and the at least one second joint structure to locally deform and shear the joining surfaces at one or more interfaces in an amount effective to form a metal-to-metal bond between the first metal and second metal of the joining surfaces. Overlaps at the joining surfaces are effective to displace surface contaminants and facilitate intimate contact between the joining surfaces without heat input.

The first metal and second metal to be cold-welded may be the same or different. They could be different alloys of the same metal. If the same metal, the first metal and the second metal may have different structural morphologies, e.g., crystal structures, grain structure, etc. Non-limiting examples of suitable metal surface materials include indium, aluminum, copper, lead, zinc, nickel, silver, palladium, cadmium, titanium, tungsten, tin, gold, or lead and combinations thereof.

Device Components and Materials

The hermetic seal formed by affixing a rupture disk to a spool piece comprises a first substrate having at least one first joint structure with a first joining surface and a second substrate having at least one second joint structure with a second joining surface, bonded at one or more interfaces by cold welding. In embodiments, the seals are biocompatible and suited for use with bioreactors, e.g., a bioreactor or other component disclosed in WO2014/095571.

In one embodiment, the two substrates may optionally contain or be incorporated in one or more of reservoirs, sensors, drugs, and electronics. The substrates may comprise, silicon, glass, Pyrex® glass, stainless steel, titanium, alumina, silicon nitride, and other biocompatible ceramics and other metals or polymers. In one embodiment, silicon substrates allow for use of optical probes in the near-infared (NIR) to infrared (IR) spectrum. It is understood that spectroscopic methods using light in the visible, UV or other wavelengths may be possible by an appropriate selection of substrate material. In addition, the substrate may comprise polymers with high enough Young's Modulus and yield stress to cause high shear during cold welding.

The joint structures have joining surfaces (also called "shear layers" or "bonding surfaces") which are preferably metal and optionally may bond to other joining surfaces. In an alternate embodiment, described in further detail below, the joining surface may be a compliant polymer. Metals with a suitably low plastic deformation stress are used as a joining surface. Suitability can be determined by one skilled in the art, for example, based on the particular joint geometry and the amount of force that can reasonably be applied to form the joint. In addition, metals that do not have a surface oxide or have a high relative oxide to parent metal hardness are preferable for use as a joining surface. See Tylecote, "Investigations on Pressure Welding" British Welding J. (March 1954) and Mohamed, et al., "Mechanism of Solid State Pressure Welding" Welding Research Supplement, pp. 302-10 (September 1975). Representative examples of suitable metals (and their alloys) include gold (Au), indium (In), aluminum (Al), copper (Cu), lead (Pb), zinc (Zn), nickel (Ni), silver (Ag), platinum (Pt), palladium (Pd), and cadmium (Cd). Representative examples of joining surface metals preferred for biocompatibility include gold and platinum.

The first joining surface may or may not be comprised of the same material as the second joining surface with which the first joining surface will form the hermetic seal. For example, the joining surfaces may be comprised of dissimilar metals or different alloys of the same parent metal. For example, the first joining surface may be gold while the second is platinum. In one embodiment, the joining surfaces are comprised of the same material with a different structural morphology. For instance, a first joining surface may be annealed to reduce the yield stress through the normal annealing mechanisms of recovery, recrystallization, and grain growth, while the second joining surface may be deposited in such a way that the grain size is small, thus increasing the yield stress.

The joining surfaces may comprise the same or a different material than the joint structures. This allows greater freedom in the fabrication method of the joint as well as more design control over the extent and location of plastic deformation. The joint structure may be comprised of a single material or a combination of materials.

Methods of Making a Hermetic Seal

In embodiments, the hermetic seals are made by compression and cold welding. In one embodiment, two substrates are hermetically sealed together by providing a first substrate having at least one first joint structure which comprises a first joining surface which is a metal, providing a second substrate having at least one second joint structure which comprises a second joining surface which is a metal, compressing together at least one first joint structure and at least one second joint structure to locally deform and shear the metal surfaces at one or more interfaces in an amount effective to form a continuous metal-to-metal bond between the joining surfaces at the one or more interfaces.

In some embodiments, ultrasonic energy may be introduced to the hermetic seal joint during the bonding process. While not being bound to any particular mechanism of action, it is believed that the ultrasonic energy may improve the hermetic seal by causing metal-to-metal inter-diffusion by scrubbing the contaminants out of the joining surfaces and deforming the surface asperities so there is intimate contact at the bonding interface.

In other embodiments where the bonding mechanism is not purely cold welding, a pulse of heat or a small increase in temperature may aid in metal bonding by increasing diffusion and lowering the metal's yield stress. For example, induction heating could be used to locally heat the joining surface metals. If other metals are present in the device and are non-magnetic, the joining metals can be selectively heated by incorporating a magnetic material under the joining surfaces.

Representative examples of magnetic materials include nickel, iron, cobalt, and combinations thereof. Alternatively, the joint structure geometry may be designed to selectively couple a magnetic field of a given frequency. (See Cao et al., "Selective and localized bonding using induction heating", Solid-State Sensor, Actuator and Microsystems Workshop, Hilton Head Island, S.C., Jun. 2-6, 2002.)

Generally, the ambient environment may be displaced with forming gas, nitrogen, vacuum, or some other condition which would minimize the rate of oxidation and contamination of the joining surfaces as the hermetic bond is formed.

Reactors/Components

The rupture disk assemblies disclosed herein can be used with a bioreactor or processing vessel or tank, or, more generally with any feed source. The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, a bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429;2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, YO, C127, L cell, COS, e.g., COS 1 and COS7, QC1-3,HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, North Carolina, USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii,*), the *Geotrichum* genus (e.g. *Geotrichum fermentans*), *Hansenula polymorpha, Yarrowia lipolytica,* or *Schizosaccharomyces*

*pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen und Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin,Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S pneumoniae pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXANTM/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1(adapted from US2016/0097074):

| Protein Product | Reference Listed Drug |
| --- | --- |
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |

| Protein Product | Reference Listed Drug |
| --- | --- |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone Antagonist | Plenaxis ™ |
| epoietin alfa | Procrit ® |

-continued

| Protein Product | Reference Listed Drug |
|---|---|
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molelcule, fusion protein, protein vaccine, or peptide as shown in Table 2, below.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | | Gonal-F, Follistim |
| | Human follicle-stimulating hormone (FSH) | Ovidrel |
| | Human chorionic gonadotropin | Luveris |
| | | GlcaGen |
| | Lutropin-α | Geref |
| | Glucagon | ChiRhoStim (human peptide), SecreFlo (porcine peptide) |
| | Growth hormone releasing hormone (GHRH) | Thyrogen |
| | Secretin | |
| | Thyroid stimulating hormone (TSH), thyrotropin | |
| Blood Clotting/Coagulation Factors | Factor VIIa | NovoSeven |
| | Factor VIII | Bioclate, Helixate, Kogenate, Recombinate, ReFacto |
| | Factor IX | |
| | Antithrombin III (AT-III) | Benefix |
| | Protein C concentrate | Thrombate III |
| | | Ceprotin |

TABLE 2-continued

Exemplary Products

| Therapeutic Product type | Product | Trade Name |
|---|---|---|
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| Blinatumomab (Blincyto ®, AMG 103, MT 103, MEDI 538, Amgen) | BiTE | CD3, CD19 | Retargeting of T cells to tumor | Approved in USA<br>Phase II and III<br>Phase II<br>Phase I | Precursor B-cell ALL<br>ALL<br>DLBCL<br>NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGFA | Blockade of 2 proangiogenics | Phase I | Solid tumors |
| RG7716 (Roche) | CrossMab | Ang2, VEGFA | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, has | Blockade of proinflammatory cytokine, binds to HSA to increase half-life | Phase II | Rheumatoid arthritis |
| ALX-0761 (Merck Serono, Ablynx) | Nanobody | IL-17A/F, has | Blockade of 2 proinflammatory cytokines, binds to HSA to increase half-life | Phase I | (Healthy volunteers) |
| ALX-0061 (AbbVie, Ablynx; | Nanobody | IL-6R, has | Blockade of proinflammatory cytokine, binds to HSA to increase half-life | Phase I/II | Rheumatoid arthritis |
| ALX-0141 (Ablynx, Eddingpharm) | Nanobody | RANKL, has | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A rupture disk comprising:

a body including an internal wall extending from a first end of the body to a second end of the body, the internal wall defining an opening extending through the body, the body further including an internal flange formed on the internal wall, the internal flange having a stepped surface;

a rupture membrane positioned within the body, the rupture membrane including a rupture membrane surface secured to the stepped surface to form a hermetic seal, the stepped surface and the rupture membrane being positioned within the body such that the rupture membrane does not extend beyond the first end of the body; and a metal-to-metal bond between a first metal of the internal flange and a second metal of the rupture membrane.

2. The rupture disk of claim 1, wherein the body is configured for removable attachment to a component.

3. The rupture disk of claim 1, wherein the body includes a first metal and the rupture membrane is fabricated from a second metal, wherein the first metal is selected from 316L stainless steel, Inconel, indium, aluminum, copper, lead, zinc, nickel, silver, palladium, cadmium, titanium, tungsten, tin, gold, and lead, and wherein the second metal is selected from 316L stainless steel, Inconel, indium, aluminum, copper, lead, zinc, nickel, silver, palladium, cadmium, titanium, tungsten, tin, gold, and lead.

4. The rupture disk of claim 1, wherein the metal-to-metal bond joins the stepped surface of the internal flange and the rupture membrane surface of the rupture membrane.

5. The rupture disk of claim 1, wherein a cold weld joins the stepped surface of the internal flange and the rupture membrane surface of the rupture membrane.

6. The rupture disk of claim 1, wherein the rupture disk is configured to form a barrier that seals an aperture of a component to which the rupture disk is attached, and wherein the rupture membrane, prior to rupture, prevents flow of a fluid out of the aperture of the component.

7. The rupture disk of claim 6, wherein the aperture is greater than 10 mm.

8. The rupture disk of claim 6, wherein the component is suitable for use in the production of a biological product.

9. The rupture disk of claim 1, wherein the body is configured for attachment to a component by a connector.

10. The rupture disk of claim 1, wherein the rupture disk is configured to be disposed between a first and second component, and wherein the rupture membrane, prior to rupture, forms a barrier between the first component and the second component.

11. The rupture disk of claim 1, wherein the body is configured as a spool piece.

12. The rupture disk of claim 1, wherein the body is configured so as to be removably attached by a clamp to a component.

13. The rupture disk of claim 1, further comprising a gasket configured to be disposed between the first end of the body and a component and to provide a fluid-proof seal there between.

14. The rupture disk of claim 1, wherein the rupture membrane is positioned such that it is entirely within the body.

15. The rupture disk of claim 1, wherein the rupture membrane is positioned such that it is entirely within the body, but close enough to the first end of the housing to minimize a volume defined by a clean surface of the rupture membrane and a portion of the internal wall between the clean surface of the rupture membrane and the first end of the body.

16. The rupture disk of claim 1, wherein the rupture membrane is positioned such that it is entirely within the body such that a volume of a space defined by a face of the rupture membrane and a portion of the internal wall between the face of the rupture membrane and the first end of the body is no more than 10 cm$^3$.

17. The rupture disk of claim 1, wherein the internal flange and the internal wall are integrally formed.

18. The rupture disk of claim 1, the rupture disk consisting of the rupture membrane and the body formed as a spool piece.

19. The rupture disk of claim 1, the rupture disk consisting essentially of the rupture membrane and the body formed as a spool piece.

20. A process system comprising a rupture disk of claim 1, wherein the process system includes a bioreactor.

21. The process system comprising a rupture disk of claim 1, wherein the process system is a bioprocess system.

22. A method of maintaining a process system comprising:

detaching a rupture disk of claim 1, from a component; and reattaching the rupture disk to the component, thereby maintaining the process system.

23. The method of claim 22, wherein the process system is a bioprocess system.

* * * * *